(12) United States Patent
Ogawa et al.

(10) Patent No.: US 8,900,152 B2
(45) Date of Patent: Dec. 2, 2014

(54) ULTRASOUND ENDOSCOPE

(71) Applicant: Olympus Medical Systems Corp., Tokyo (JP)

(72) Inventors: Tomoaki Ogawa, Machida (JP); Kenichi Nishina, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/015,000

(22) Filed: Aug. 30, 2013

(65) Prior Publication Data

US 2014/0046190 A1 Feb. 13, 2014

Related U.S. Application Data

(63) Continuation of application No. PCT/JP2013/061455, filed on Apr. 18, 2013.

(30) Foreign Application Priority Data

Jul. 4, 2012 (JP) ................................. 2012-150737

(51) Int. Cl.
*A61B 8/14* (2006.01)
*A61B 8/12* (2006.01)
*A61B 1/07* (2006.01)
*A61B 8/00* (2006.01)
*A61B 1/005* (2006.01)

(52) U.S. Cl.
CPC ... *A61B 8/12* (2013.01); *A61B 1/07* (2013.01); *A61B 8/4444* (2013.01); *A61B 8/445* (2013.01); *A61B 8/56* (2013.01); *A61B 1/005* (2013.01)
USPC ........... 600/459; 600/424; 600/407; 600/437; 600/101; 600/109

(58) Field of Classification Search
None
See application file for complete search history.

(56) References Cited

U.S. PATENT DOCUMENTS

| 2009/0088631 A1 | 4/2009 | Dietz et al. |
| 2009/0292199 A1 | 11/2009 | Bielewicz et al. |
| 2010/0280316 A1 | 11/2010 | Dietz et al. |
| 2011/0249106 A1 | 10/2011 | Makino et al. |

FOREIGN PATENT DOCUMENTS

| JP | 62-272222 A | 11/1987 |
| JP | 2003-102732 A | 4/2003 |
| JP | 2005-218519 A | 8/2005 |
| JP | 2009-039433 A | 2/2009 |
| JP | 2010-016076 A | 1/2010 |
| JP | 2010-531718 A | 9/2010 |
| JP | 2011-525842 A | 9/2011 |
| JP | 2011-217887 A | 11/2011 |
| WO | WO 2009/006335 A1 | 1/2009 |
| WO | WO 2009/158012 A2 | 12/2009 |
| WO | WO 2011/085166 A1 | 7/2011 |

*Primary Examiner* — Joel Lamprecht
(74) *Attorney, Agent, or Firm* — Scully, Scott, Murphy & Presser, PC

(57) ABSTRACT

An ultrasound endoscope having an ultrasound probe that is provided at a rigid portion at a distal end of an insertion portion, a cable that transmits electrical signals to and from the ultrasound probe, and a rigid flexible substrate that is interposed between the ultrasound probe and the cable to transmit the electrical signals, and configures a part of a planar member in which a plurality of layers including a wiring layer are stacked as a flexible portion further including an insulating layer, and the other portion as a rigid portion further including a rigid layer, wherein the ultrasound probe is connected to the rigid portion, and at least a part of the flexible portion is disposed in a spiral shape to surround a wiring connection portion of the cable and the rigid flexible substrate, and an uncovered portion of a distal end side of the cable.

7 Claims, 8 Drawing Sheets

ULTRASOUND ENDOSCOPE

CROSS REFERENCE TO RELATED APPLICATION

This application is a continuation application of PCT/JP2013/061455 filed on Apr. 18, 2013 and claims benefit of Japanese Application No. 2012-150737 filed in Japan on Jul. 4, 2012, the entire contents of which are incorporated herein by this reference.

BACKGROUND OF THE INVENTION

1. Field of the Invention

The present invention relates to an ultrasound endoscope that includes an ultrasound probe at a distal end side rigid portion of an insertion portion.

2. Description of the Related Art

Ultrasound endoscopes include a linear type and a convex type of ultrasound endoscope. An ultrasound probe that is mounted on a convex type ultrasound endoscope out of the above ultrasound endoscopes is placed onto an electric substrate (hereinafter called a transducer substrate) that is configured as, for example, a rigid substrate.

Figure 12:
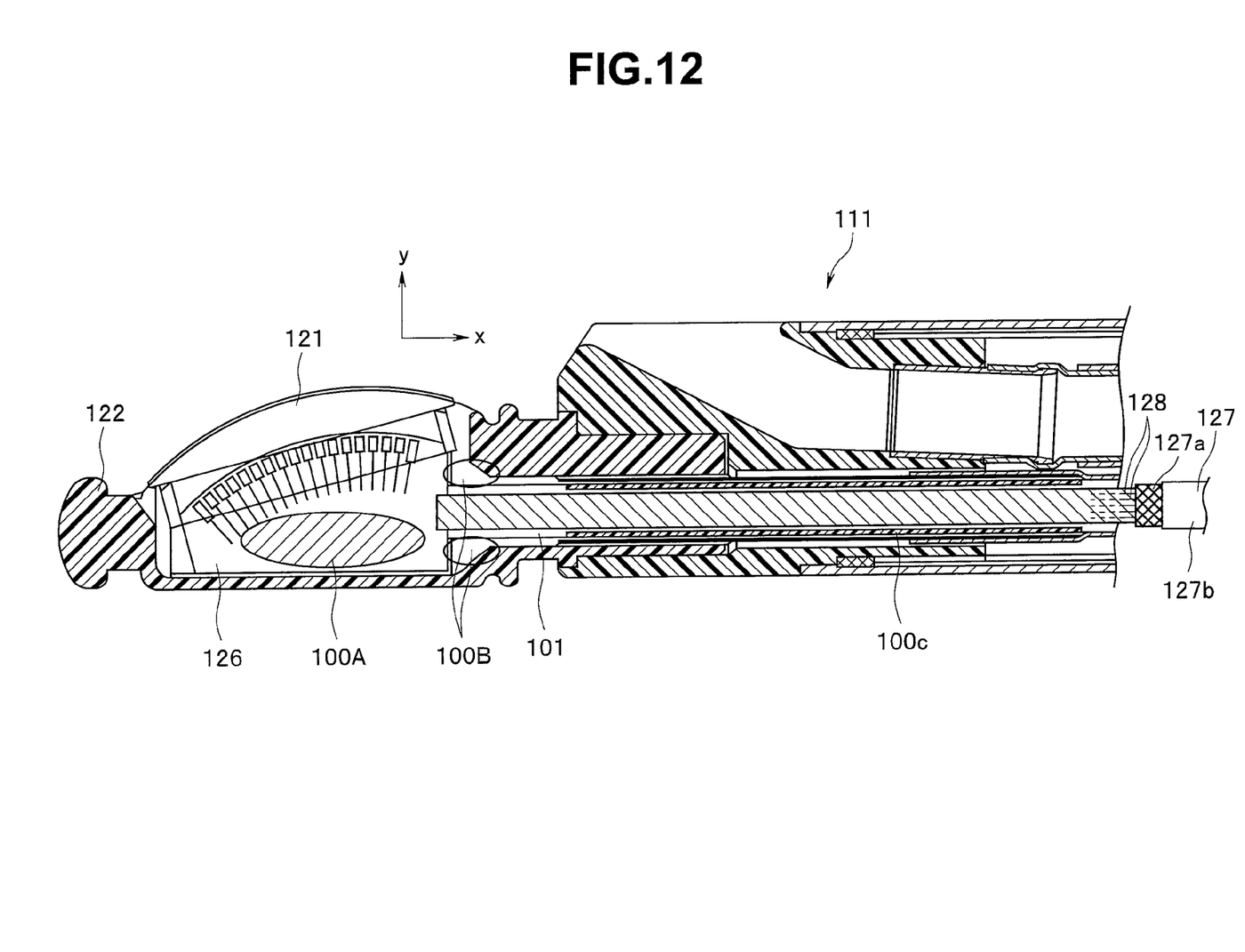
FIG. 12 is a sectional view showing an ultrasound probe placed at a distal end portion of a conventional ultrasound endoscope via a rigid substrate.

FIG. 12 is a sectional view showing an ultrasound probe that is placed at a distal end portion of a conventional ultrasound endoscope via a rigid substrate.

An ultrasound probe 121 has a convex type configuration integrally provided with an acoustic lens and the like, and is electrically connected to a transducer substrate 126 configured by a rigid substrate. The transducer substrate 126 is placed adjacently to a proximal end side of a nose piece 122 provided at the most distal end of an endoscope distal end portion.

Further, electric signals that are inputted to and outputted from the ultrasound probe 121 are transmitted via a cable 127. The cable 127 is configured by a plurality of signal lines 128 being covered with an overall shield 127a that has an electromagnetic wave shielding function, and a cable sheathing cover 127b having insulation properties. The cable 127 is such that in a proximal end side of a rigid portion 111 (an x-axis normal direction side), the cable sheathing cover 127b and the overall shield 127a are removed, and thereafter, the respective signal lines 128 are inserted to a transducer substrate 126 side via an insertion hole 101 provided in the rigid portion 111.

In the configuration as above, the respective signal lines 128 are connected to the transducer substrate 126 by soldering or the like, and therefore, the transducer substrate 126 needs a space 100A for soldering as illustrated. Accordingly, a height (a width in a y-axis direction) in FIG. 12 of the transducer substrate 126 is as illustrated in the drawing.

Further, in order to perform work of connecting the signal line 128 to the transducer substrate 126, a margin is required in the length of the signal line 128, and in order to extract the transducer substrate 126 which is still wired from the installation section for a repair or the like to be done at some future date, a margin is also required in the length of the signal line 128. Accordingly, the signal line 128 is configured to be somewhat long, and a space 100B for storage of an excessive length of the signal line 128 is required as illustrated in the drawing.

Furthermore, since the respective signal lines 128 have the cable sheathing cover 127b with insulating properties removed inside the insertion hole 101, an additional insulating member 100C configured by, for example, a polyimide pipe or the like is placed in the insertion hole 101, and the respective signal lines 128 are disposed in the insulating member 100C, in order to ensure insulating properties (voltage resistance) at a predetermined level of the signal lines 128 that is required in protection against electrical hazard.

Further, in place of the configuration in which the cable for transmitting electrical signals that are inputted to and outputted from the ultrasound probe is connected to the transducer substrate configured by a rigid substrate as described above, a configuration is also proposed, in which a flexible printed substrate is further provided, and a cable is connected to the flexible printed substrate.

For example, FIG. 1, FIG. 4 and the like of Japanese Patent Application Laid-Open Publication No. 2005-218519 indicate that in a convex type ultrasound endoscope, a rigid portion (9) and a bending portion (10) are provided to connect to an ultrasound transducer unit (20) at an insertion portion (2a) distal end, and that the ultrasound transducer unit (20) is configured to electrically connect an ultrasound transmission/reception portion (21) to a rigid substrate (35), and further electrically connect to a signal cable bundle (29) via a flexible printed substrate (33). In addition, Japanese Patent Application Laid-Open Publication No. 2005-218519 describes protecting connecting portions by folding the flexible printed substrate (33) to prevent the connecting portions of respective electrode portions (33b) of the flexible printed substrate (33) and respective signal core wires (29a) of the signal cable bundle (29) from being exposed to an outside.

Since a flexible printed substrate can change the shape thereof, the flexible printed substrate is folded in the above described Japanese Patent Application Laid-Open Publication No. 2005-218519, and as another shape change example, Japanese Patent Application Laid-Open Publication No. 2003-102732 is cited. FIG. 1 and the like of Japanese Patent Application Laid-Open Publication No. 2003-102732 describe an ultrasound probe (10) including an ultrasound transducer (20) for radial electronic scanning in which a number of ultrasound transducers (30) are arranged in a circumferential direction. The ultrasound probe (10) is used by being inserted through the inside of a treatment instrument insertion channel (6) of an endoscope (1), but since a diameter of the ultrasound transducer (20) is larger than a diameter of the treatment instrument insertion channel (6), a proximal end side of a flexible cord (22) provided with the ultrasound transducer (20) at a distal end side is inserted through the treatment instrument insertion channel (6). It is indicated that at this time, the flexible substrate (33) is connectively provided in an inclined direction at the proximal end side of the flexible cord (22) as shown in FIG. 2, FIG. 3 and the like, and in order to insert the flexible substrate (33) through the inside of the treatment instrument insertion channel (6) of the endoscope (1), the flexible substrate (33) is spirally wound into a cylindrical shape and is inserted into a sheath member (38). After the flexible substrate (33) is inserted through the treatment instrument insertion channel (6), the sheath member (38) is removed, and the flexible substrate (33) is developed to be connected to an ultrasound observation apparatus (11) via relay means (13).

Incidentally, there is proposed a rigid flexible substrate in which a rigid substrate and a flexible substrate are integrated, and as a configuration example thereof, Japanese Patent Application Laid-Open Publication No. 2010-16076 is cited. Japanese Patent Application Laid-Open Publication No. 2010-16076 describes a multilayer rigid flexible printed substrate including rigid portions (2A) and (2B) at both ends of a flexible printed substrate portion (1). As shown in FIG. 2 and FIG. 3, the multilayer rigid flexible printed substrate is of a stacked structure having a top coat layer (3) with electrical conductivity, a silver paste layer (4), copper foil (6) that has a pattern formed by etching and functions as a signal line and a GND pattern, a polyimide layer (7), and a cover lay (8). Out of the respective layers, the top coat layer (3) with electrical conductivity and the silver paste layer (4) are provided from the viewpoint of EMC (electro-magnetic compatibility), and function as shields.

Figure 13:
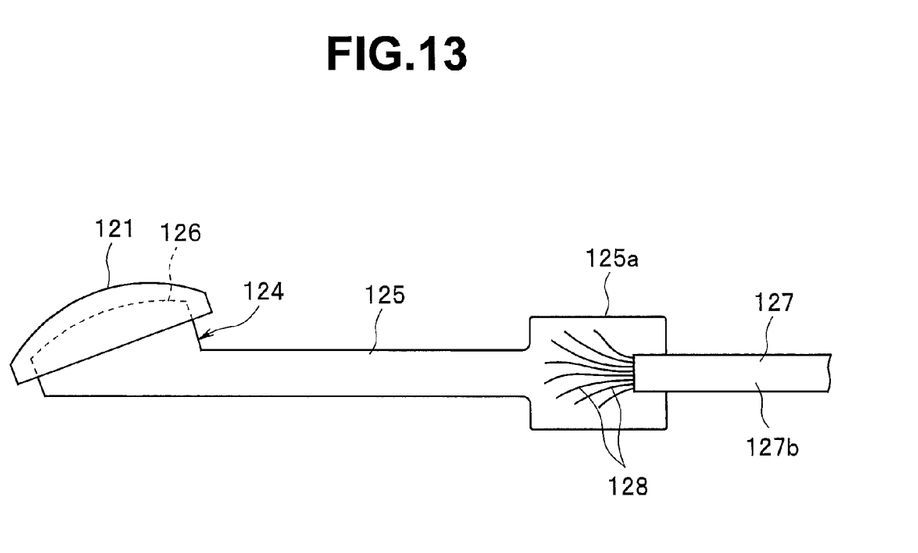
FIG. 13 is a view showing a substrate connection structure of an ultrasound probe using a conventional rigid flexible substrate.

FIG. 13 is a view showing a substrate connection structure of an ultrasound probe using a conventional rigid flexible substrate.

The ultrasound probe 121 is connected to the transducer substrate 126 that is configured by a rigid substrate in a rigid flexible substrate 124. From the transducer substrate 126, a flexible substrate portion 125 is extensively provided at a proximal end side, and a cable connection portion 125a is provided at a proximal end of the flexible substrate portion 125. The respective signal lines 128 of the cable 127 are connected to the cable connection portion 125a by soldering or the like.

If the configuration as above is used, the height of the transducer substrate 126 can be restrained, and reduction in diameter of the portion provided with the ultrasound probe in the endoscope distal end portion can be achieved as a result. Further, since connection of the respective signal lines 128 can be performed in the cable connection portion 125a at the proximal end side apart from the ultrasound probe 121, a working space at the time of wiring also can be ensured.

SUMMARY OF THE INVENTION

An ultrasound endoscope according to one aspect of the present invention has an insertion portion that is insertable into an observation site, and is provided with a rigid portion at a distal end side, an ultrasound probe that is provided at the rigid portion, and has a plurality of ultrasound transducers that transmit and receive ultrasound signals, a cable for transmitting electrical signals that are inputted to and outputted from the ultrasound probe, and a rigid flexible substrate that is interposed between the ultrasound probe and the cable to transmit the electrical signals, is configured as a planar member in which a plurality of layers including a wiring layer are stacked, and has a flexible portion configured only by a flexible substrate, and a rigid portion provided with a rigid substrate, by forming a part of the planar member as the flexible substrate which further includes an insulating layer, and by forming the other part of the planar member as the rigid substrate which further includes a rigid layer, wherein the ultrasound probe is connected to the rigid portion, and at least a part of the flexible portion is disposed in a spiral shape to surround a wiring connection portion of the cable and the rigid flexible substrate, and an uncovered portion of a distal end side of the cable.

DETAILED DESCRIPTION OF THE PREFERRED EMBODIMENTS

Hereinafter, embodiments of the present invention will be described with reference to the drawings.

Embodiment 1

Figure 1:
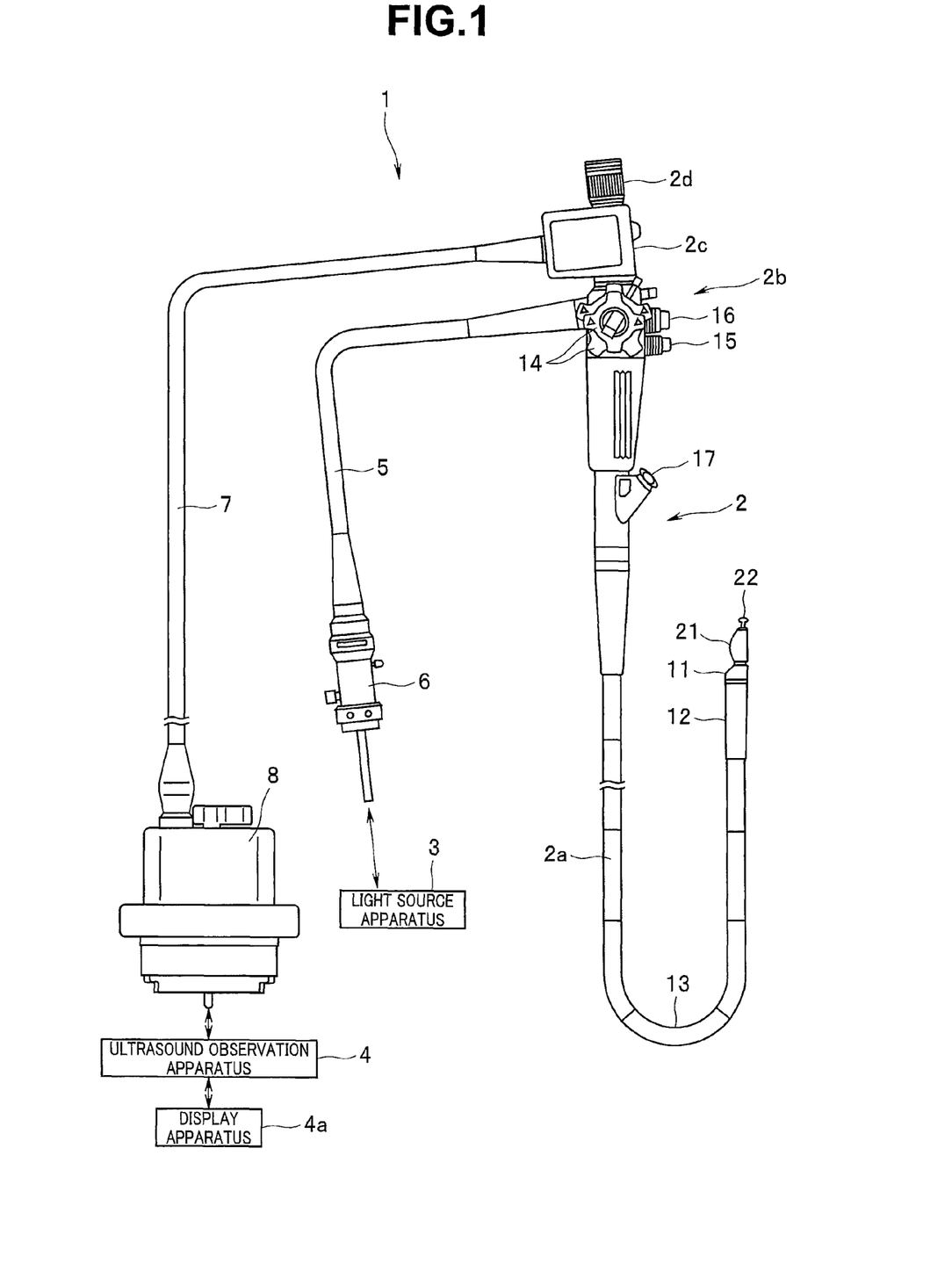
FIG. 1 is a view showing a configuration of an ultrasound endoscope diagnostic apparatus including an ultrasound endoscope, in embodiment 1 of the present invention.

FIG. 1 to FIG. 5 show embodiment 1 of the present invention, and FIG. 1 is a view showing a configuration of an ultrasound endoscope diagnostic apparatus including an ultrasound endoscope.

As shown in FIG. 1, an ultrasound endoscope diagnostic apparatus 1 includes an ultrasound endoscope 2 including an ultrasound probe 21 at a distal end portion of an insertion portion 2a that is inserted into a body cavity, a light source apparatus 3 that supplies an illuminating light to an illumination optical system contained in the ultrasound endoscope 2, an ultrasound observation apparatus 4 that generates an ultrasound drive signal that is supplied to the ultrasound probe 21, and performs processing of a signal obtained from ultrasound received by the ultrasound probe 21 and the like, and a display apparatus 4a that receives an image signal generated and outputted by the ultrasound observation apparatus 4 and displays an ultrasound diagnostic image.

The ultrasound endoscope 2 and the light source apparatus 3 are detachably connected via an endoscope connector 6 that is provided at a proximal end of a universal cord 5. Further, the ultrasound endoscope 2 and the ultrasound observation apparatus 4 are detachably connected via an ultrasound connector 8 that is provided at a proximal end of an ultrasound cord 7.

The ultrasound endoscope 2 includes the insertion portion 2a that is formed into an elongated shape and is inserted into a body cavity, an operation portion 2b that is connectively provided at a proximal end side of the insertion portion 2a, a relay portion 2c that is connectively provided at a proximal end side of the operation portion 2b, and an eyepiece portion 2d that is connectively provided at a proximal end side of the relay portion 2c. From a side portion of the operation portion 2b, the aforementioned universal cord 5 is extended, and from a side portion of the relay portion 2c, the aforementioned ultrasound cord 7 is extended.

The insertion portion 2a is insertable into an observation site, and includes a rigid portion 11 at a distal end side. A main body of the rigid portion 11 is formed ob a resin material excellent in chemical resistance, biocompatibility and insulating properties, for example, polysulfone, polyethyletherketone, or the like. In the rigid portion 11, a nose piece 22 is provided at the most distal end, and the ultrasound probe 21 is connectively provided at a proximal end side of the nose piece 22.

At a proximal end side of the rigid portion 11, a bending portion 12 bendable in, for example, an up and down and a left and right directions is connectively provided. Further, between a proximal end side of the bending portion 12 and a distal end side of the operation portion 2b, a flexible portion 13 with a small diameter having a long length and flexibility is placed.

The operation portion 2b is provided with an angle knob 14 for performing a bending operation of the bending portion 12 in a desired direction, an air/water feeding button 15 for performing an air feeding and a water feeding operations, a suction button 16 for performing a suction operation, a treatment instrument insertion port 17 for introducing a treatment instrument or the like into a body cavity, and the like.

Figure 2:
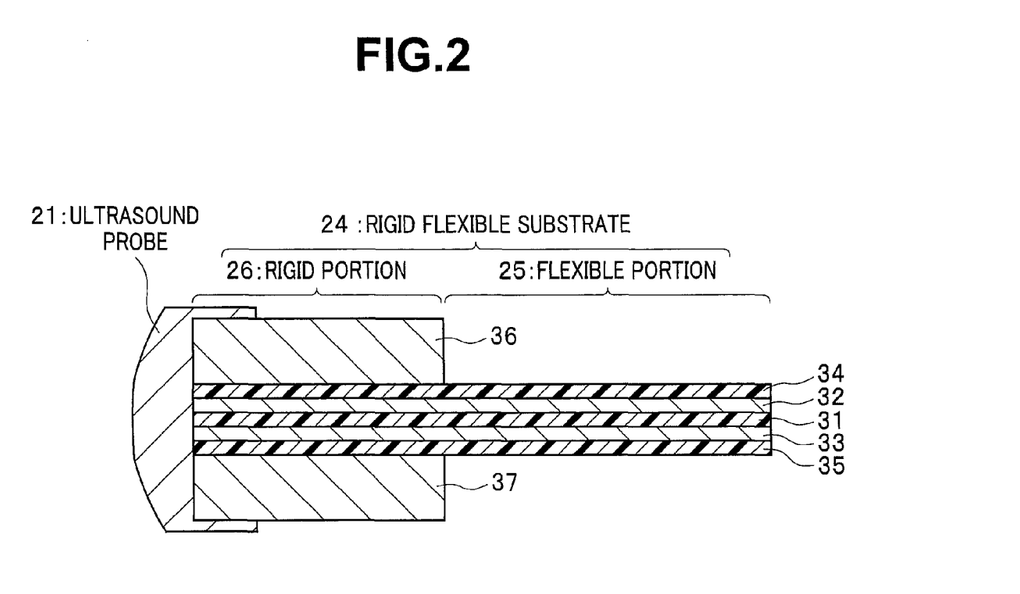
FIG. 2 is a view showing an outline of a stacked structure of a rigid flexible substrate connected to an ultrasound probe in the above described embodiment 1 of the present invention.

Next, FIG. 2 is a view showing an outline of a stacked structure of a rigid flexible substrate 24 that is connected to the ultrasound probe 21.

The rigid flexible substrate 24 has a flexible portion 25 including a structure as a flexible substrate, and a rigid portion 26 including a structure as a rigid substrate.

First, the ultrasound probe 21 is connected to the rigid portion 26 in the rigid flexible substrate 24. The ultrasound probe 21 is such that an ultrasound transducer group configured by a plurality of piezoelectric elements (piezoelectric type) or air-gaps (electrostatic capacitance type) sandwiched between electrodes being arranged, and an acoustic lens that gives directivity to ultrasound signals that are transmitted and received from the ultrasound transducer group are integrally configured.

The flexible portion 25 has a stacked structure in which a wiring layer 32 on which a wiring pattern by copper foil is formed, and a shield layer 33 including a function of shielding electromagnetic waves are formed onto a base layer 31 configured by, for example, polyimide or the like and having insulating properties, an insulating layer 34 is formed on an outer side of the wiring layer 32, and an insulating layer 35 is formed on an outer side of the shield layer 33, respectively. Here, the wiring layer 32 reaches an inside of the rigid portion 26. Further, at least the shield layer 33 reaches a distal end face via the inside of the rigid portion 26, and is thermally connected to the ultrasound probe 21. Accordingly, the shield layer 33 includes a function of transmitting heat generated from the ultrasound probe 21 when the ultrasound probe 21 transmits and receives ultrasound, and can contribute to cooling of the ultrasound probe 21.

The rigid portion 26 has a rigid substrate structure by glass epoxy substrates 36 and 37 as rigid layers formed on, for example, both surfaces of the stacked structure as described above. Wiring patterns are also formed on the glass epoxy substrates 36 and 37, and the wiring patterns on the glass epoxy substrates 36 and 37 and the wiring pattern on the wiring layer 32 of the flexible portion 25 are connected by formation of, for example, vias (through-holes in a thickness direction and the like), but illustration and the detailed description of the configuration are omitted since the configuration is an ordinary configuration.

As above, the rigid flexible substrate 24 is configured as a planar member in which a plurality of layers including a wiring layer are stacked, and a part of the planar member is formed by a flexible substrate which further includes an insulating layer, whereas the other part of the planar member is formed by a rigid substrate which further includes a rigid layer, whereby the rigid flexible substrate 24 which includes the flexible portion 25 configured only by the flexible substrate, and the rigid portion 26 provided with the rigid substrate.

Note that the structure of the rigid flexible substrate 24 described above is only one example, and a rigid flexible substrate with another optional configuration may be adopted as a matter of course.

Figure 3:
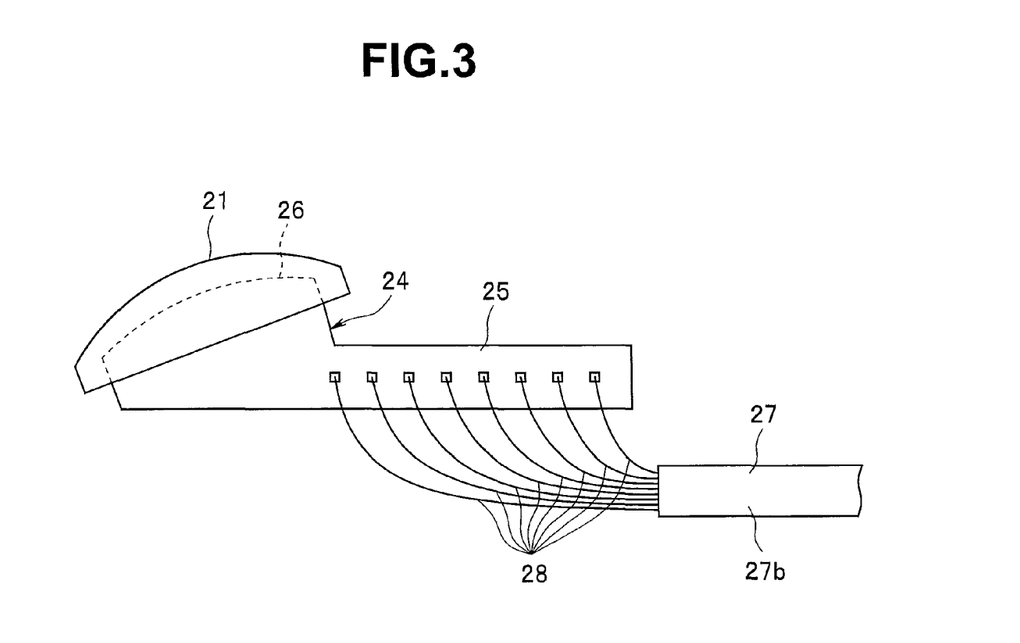
FIG. 3 is a view showing an example of connecting a cable to a flexible portion of the rigid flexible substrate, in the above described embodiment 1 of the present invention.

FIG. 3 is a view showing an example of connecting a cable 27 to the flexible portion 25 of the rigid flexible substrate 24.

The cable 27 transmits electric signals that are inputted to and outputted from the ultrasound probe 21. The cable 27 is configured by a plurality of signal lines 28 being covered with an overall shield 27a having an electromagnetic wave shielding function (see FIG. 10, FIG. 11 and the like), and a cable sheathing cover 27b having insulating properties. Here, the overall shield 27a is connected to a ground.

Further, the flexible portion 25 is extensively provided in, for example, a band shape toward a proximal end side from the rigid portion 26 to which the ultrasound probe 21 is connected. When wiring connection is performed, the cable sheathing cover 27b and the overall shield 27a at a distal end side of the cable 27 are removed, and thereby, the signal lines 28 are exposed to an uncovered portion. Next, the exposed signal lines 28 are electrically connected to electric contacts formed on the wiring layer 32 of the flexible portion 25 by soldering or the like, and thereby a wiring connection portion is configured. At this time, the aforementioned shield layer 33 is connected to the signal line 28 that is connected to the ground out of a plurality of signal lines 28. Accordingly, heat that is generated from the ultrasound probe 21 and is transmitted through the shield layer 33, a current that is generated by electromagnetic waves shielded by the shield layer 33 and the like are transmitted from the signal line 28 connected to the ground.

In this manner, the rigid flexible substrate 24 is interposed between the ultrasound probe 21 and the cable 27 to transmit electrical signals.

Since connection of the plurality of signal lines 28 and the flexible portion 25 can be performed at a plurality of spots along a longitudinal direction of the flexible portion 25, connecting work is easy, and a width of the band shape of the flexible portion 25 does not have to be made large.

Figure 4:
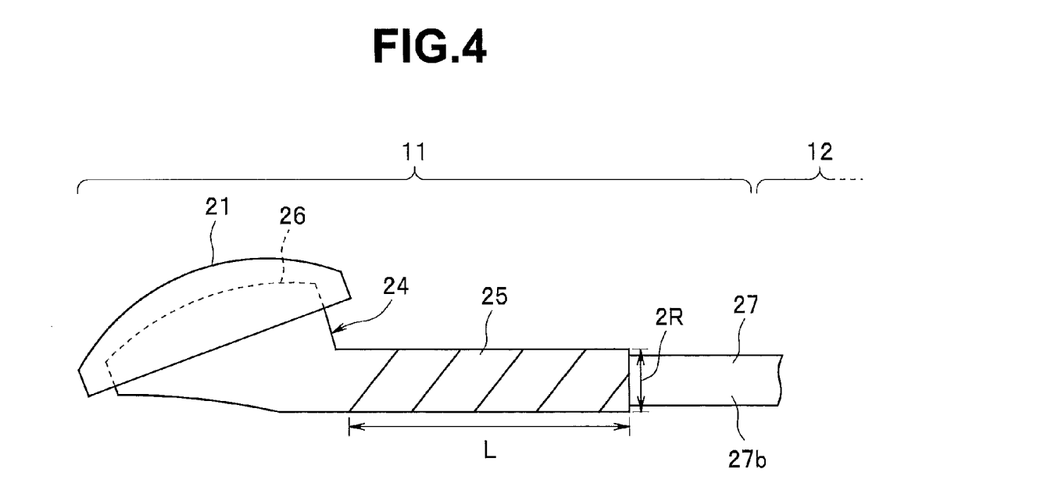
FIG. 4 is a view showing a shape of the flexible portion at a time of being stored in a rigid portion, in the above described embodiment 1 of the present invention.

The flexible portion 25 to which the plurality of signal lines 28 are connected in this manner is deformed into a shape as shown in FIG. 4 when the flexible portion 25 is stored into an insertion hole or the like in the rigid portion 11. FIG. 4 is a view showing the shape of the flexible portion 25 when the flexible portion 25 is stored in the rigid portion 11.

Namely, at least a part of the flexible portion 25 (most part except for a distal end side near the rigid portion 26, of the band-shaped portion extensively provided from the rigid portion 26, in the example shown in FIG. 4) is disposed in a spiral shape (spiral) to surround the aforementioned wiring connection portion of the cable 27 and the flexible portion 25. A spiral portion of the flexible portion 25 is disposed to also surround the uncovered portion by being further wound on the uncovered portion at the distal end side of the cable 27. At this time, in order to inhibit unwinding of a wound portion, it is conceivable to fix, for example, a proximal end portion of the flexible portion 25 to the distal end side of the cable 27 with use of an adhesive (however, the configuration of prevention of unwinding is not limited thereto).

The rigid flexible substrate 24 that is deformed into the shape as shown in FIG. 4 is disposed only in the rigid portion 11, and is not disposed in the bending portion 12. Since the bending portion 12 is a site that is freely bent vertically and laterally as described above, if the rigid flexible substrate 24 is disposed in the bending portion 12, a flexural load (stress) is applied at the time of bending, and the flexible portion 25 that is in the spiral shape is deformed. Since the wiring connection portion is stored in the flexible portion 25 that is in the spiral shape, if the deformation like this is applied in various directions for a long time period, it is not preferable from the viewpoint of durability. Therefore, the rigid flexible substrate 24 is disposed only in the rigid portion 11.

Figure 5:
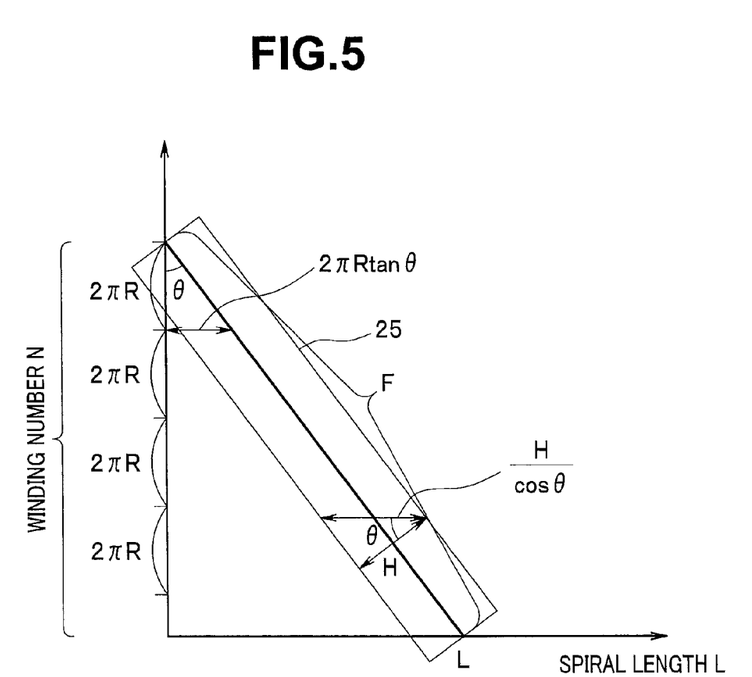
FIG. 5 is a diagram for explaining a relationship of a dimension of the flexible portion itself, and a dimension after being disposed in a spiral shape, in the above described embodiment 1 of the present invention.

Subsequently, details of the dimensions and the like when the flexible portion 25 is disposed in the spiral shape at constant pitches will be described with reference to FIG. 5. FIG. 5 is a diagram for explaining a relationship of the dimension of the flexible portion 25 itself, and a dimension after the flexible portion 25 is disposed in the spiral shape.

First, a length of the band-shaped portion that is an object to be disposed in the spiral shape in the flexible portion 25 is set as F, and a width thereof is set as H. Further, a radius (a spiral radius) of a cylinder after the band-shaped portion is disposed in the spiral shape is set as R, a length thereof (a spiral length) is set as L, and a number of windings in the spiral shape is set as N. The flexible portion 25 is wound around in such a manner that a center axis of the cylinder after the band-shaped portion is disposed in the spiral shape becomes parallel with a horizontal axis in FIG. 5. At this time, FIG. 5 can be considered as a development view of the flexible portion 25 disposed in the spiral shape. Further, $\theta$ shown in FIG. 5 represents an inclination angle that the longitudinal direction of the band shape of the flexible portion 25 forms with respect to the center axis of the cylinder.

First, if under a certain radius R, the winding number N is decreased, and the inclination angle $\theta$ is made an angle close to 90°, a gap is likely to occur between the band-shaped flexible portions 25 disposed in the spiral shape. Such a gap is not favorable from the viewpoint of the insulating properties and shieldability. Therefore, a condition for preventing occurrence of the gap is obtained first. The condition is obtained as a condition that a cylinder length $2\pi R \tan \theta$ at the time of the flexible portion 25 being wound around one time is not more than a width H of the flexible portion 25 in the center axis direction of the cylinder/$\cos \theta$, and is as the following expression 1.

$$2\pi R \tan \theta \leq H/\cos \theta \quad \text{[Expression 1]}$$

Here, for the inclination angle $\theta$, the relation of the following expression 2 is established.

$$\sin \theta = L/F \quad \text{[Expression 2]}$$

Accordingly, when expression 1 is transformed as a conditional expression with respect to the spiral length L with use of expression 2, the result is as shown in the following expression 3.

$$L \leq HF/2\pi R \quad \text{[Expression 3]}$$

The numerator HF of expression 3 represents an area of the band-shaped portion that is an object to be disposed in the spiral shape in the flexible portion 25. Further, the denominator $2\pi R$ of expression 3 represents an outer circumferential length (a spiral outer circumferential length) of the cylinder after the band-shaped portion is disposed in the spiral shape. Accordingly, if some transformation is performed for expression 3, expression 3 can be roughly expressed as the following expression 4.

$$L \times \text{(spiral outer circumferential length)} = \text{(spiral area)} \leq \text{(flexible portion area)} \quad \text{[Expression 4]}$$

Namely, it is understandable that the spiral length L needs to be set so that the area (the spiral area) of the circumferential face of the cylinder after the band-shaped portion is disposed in the spiral shape does not exceed the area of the flexible portion 25.

Next, the length L of the cylinder after the band-shaped portion is disposed in the spiral shape needs to be a certain length (the length is set as L0) that is obtained in design based on the length of the rigid portion 11. The winding number N to achieve the length L0 will be considered. First, the winding number N becomes maximum when $\theta=0°$, and therefore, a range the winding number N can take is as shown in the following expression 5.

$$0 < N \leq F/2\pi R \quad \text{[Expression 5]}$$

Here, at the time of N=0, the disposition cannot be said as spiral disposition, and therefore, N=0 is excluded.

When Pythagorean theorem is applied to the triangle shown in FIG. 5 at the time of L=L0 under the condition shown in expression 5, the following expression 6 is established with respect to the winding number N.

$$N = \sqrt{[F^2 - (L0)^2]}/2\pi R \quad \text{[Expression 6]}$$

Here, $\sqrt{[\ ]}$ represents a square root of the content in [ ], and $^2$ represents square. Accordingly, the flexible portion 25 can be disposed in the spiral shape so that the winding number becomes the winding number N shown in expression 6.

Further, a condition that is imposed on the length F and the width H of the flexible portion 25 in order to achieve the length L0 without generating the aforementioned gap, and without overlaying the flexible portion 25 wastefully with redundancy is as the following expression 7.

$$HF = 2\pi R L0 \quad \text{[Expression 7]}$$

With reference to the respective conditional expressions as above, the length F and the width H of the flexible portion 25 are designed, and the winding number N, the inclination angle $\theta$ (or further, the radius R and the spiral length L) and the like can be determined.

According to embodiment 1 as above, wiring to the ultrasound probe 21 is performed via the rigid flexible substrate 24, and at least a part of the flexible portion 25 in the rigid flexible substrate 24 is disposed in the spiral shape to surround the wiring connection portion of the cable 27 and the flexible portion 25, whereby insulating properties of the wiring connection portion can be ensured. At this time, an additional polyimide pipe or the like is not required, and therefore, reduction in diameter of the rigid portion 11 can be also achieved.

Further, since the flexible portion 25 further includes the shield layer 33 in a plurality of layers, the shieldability of the wiring connection portion can be also ensured, and a more favorable ultrasound image can be obtained. At this time, an additional shield member is not required, and therefore, reduction in diameter of the rigid portion 11 can be achieved.

Further, at least a part of the flexible portion 25 is disposed in the spiral shape to surround the uncovered portion of the distal end side of the cable 27, and therefore, insulating properties and shieldability also can be ensured for the uncovered portion. Further, the flexible portion 25 is wound around the uncovered portion of the distal end side of the cable 27, whereby fixing or the like by an adhesive is enabled, and unwinding can be also prevented.

Furthermore, since the wiring connection portion is not provided in the vicinity of the rigid portion 26 to which the ultrasound probe 21 is connected, the height of the rigid portion 26 is restrained, and reduction in diameter of the rigid portion 11 can be achieved.

In addition, since the shield layer 33 in a plurality of layers that are stacked is thermally connected to the ultrasound probe 21, the shield layer 33 transmits and radiates heat that is generated from the ultrasound probe 21, and can contribute to cooling of the ultrasound probe 21.

Moreover, since the rigid flexible substrate 24 is disposed only in the rigid portion 11, the flexure load (stress) by the bending portion 12 that is received by the wiring connection portion can be reduced as much as possible, and durability can be ensured.

Furthermore, the flexible portion 25 itself to which the signal line 28 is connected is only disposed in the spiral shape, whereby the insulating structure and the shielding structure can be configured, and therefore, the advantage that assembly is easy and workability is high is provided. Further, the wiring connection portion of the signal line 28 and the flexible portion 25, and the excessive length of the signal line 28 also can be easily stored in the rigid portion 11. Moreover, the flexible portion 25 disposed in the spiral shape has the advantage of being able to be easily inserted through the insertion hole or the like in the rigid portion 11.

Embodiment 2

Figure 6:
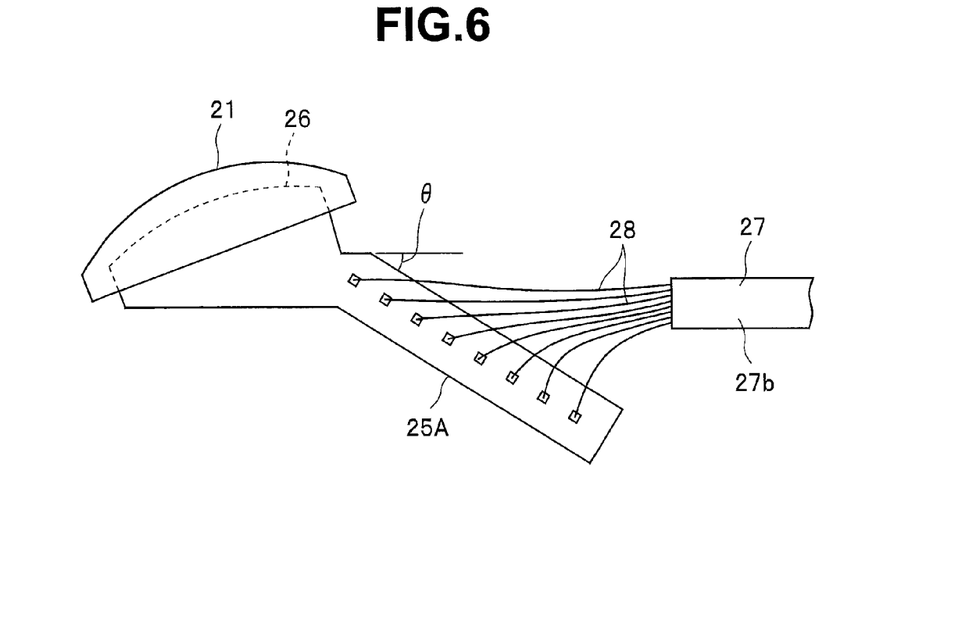
FIG. 6 is a view showing a configuration of a flexible portion in a rigid flexible substrate, in embodiment 2 of the present invention.
Figure 7:
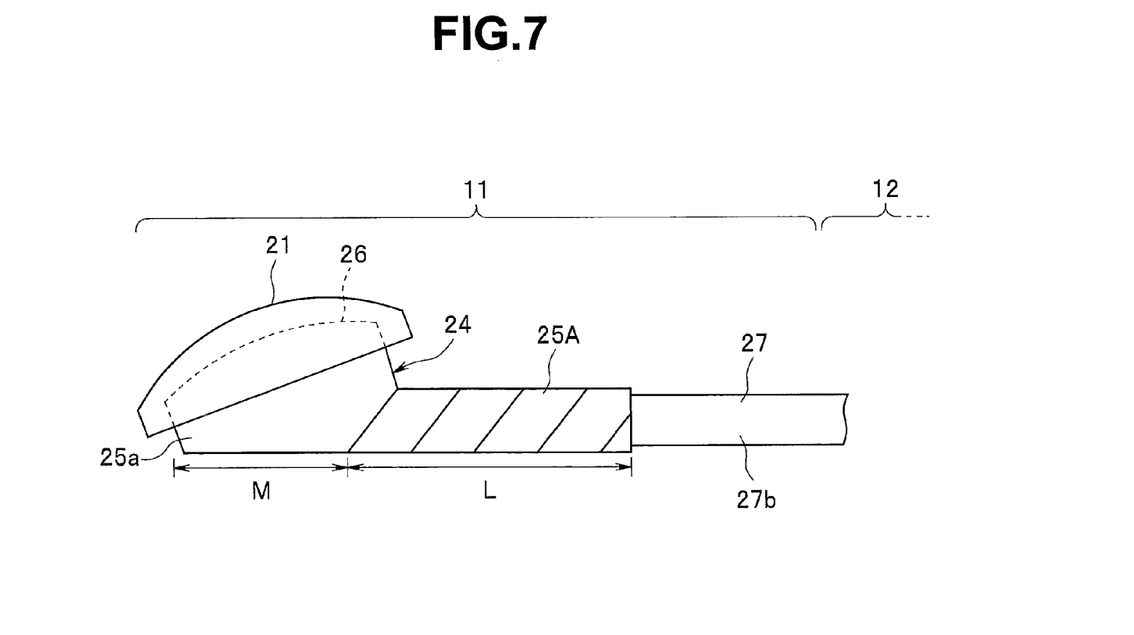
FIG. 7 is a view showing a shape of the flexible portion at a time of being stored in a rigid portion, in the above described embodiment 2 of the present invention.

FIG. 6 and FIG. 7 show embodiment 2 of the present invention. FIG. 6 is a view showing a configuration of a flexible portion 25A in the rigid flexible substrate 24. FIG. 7 is a view showing a shape of the flexible portion 25A at a time of the flexible portion 25A being stored in the rigid portion 11.

In embodiment 2, parts similar to those of the aforementioned embodiment 1 are assigned with the same reference signs, the description thereof is properly omitted, and only a different point will be mainly described.

The flexible portion 25 shown in FIG. 3 of the aforementioned embodiment 1 is extended toward a proximal end side in the axial direction of the insertion portion 2a from the rigid portion 26. In contrast with this, the flexible portion 25A of the present embodiment is extended to an oblique direction of the proximal end side from the rigid portion 26 so as to form the angle θ with respect to the axial direction of the insertion portion 2a as shown in FIG. 6.

Here, the angle θ the most desirably corresponds to the inclination angle θ described in embodiment 1. By the flexible portion 25A being formed as above, an axis center of a cylinder configured by the flexible portion 25A being disposed in the spiral shape naturally corresponds to the axial direction of the insertion portion 2a. Accordingly, unnatural twist or the like does not occur to a flexible distal end portion 25a near the rigid portion 26 of the flexible portion 25A.

In contrast with this, in the case of the configuration of embodiment 1, in order to cause the flexible portion 25 disposed in the spiral shape to correspond to the axial direction of the insertion portion 2a, a portion near the rigid portion 26, of the flexible portion 25 needs to be curved, and in order to avoid stress and a load in the case of a curvature being small, the length of the portion which is not disposed in the spiral shape in the flexible portion 25 needs to be ensured to some degree.

In contrast with the above, according to the configuration of the present embodiment, a length M of the flexible distal end portion 25a as shown in FIG. 7 can be shortened more than in the configuration of the aforementioned embodiment 1.

According to embodiment 2 as above, a substantially similar effect to that of the aforementioned embodiment 1 is provided, unnatural curve does not occur to the flexible distal end portion 25a, and in addition, shortening of the flexible portion 25A also can be achieved. Accordingly, the length of the flexible portion 25A after the flexible portion 25A is disposed in the spiral shape also can be shortened. Thereby, the rigid portion 11 also can be shortened, which can contribute to miniaturization of the endoscope distal end portion.

Embodiment 3

Figure 8:
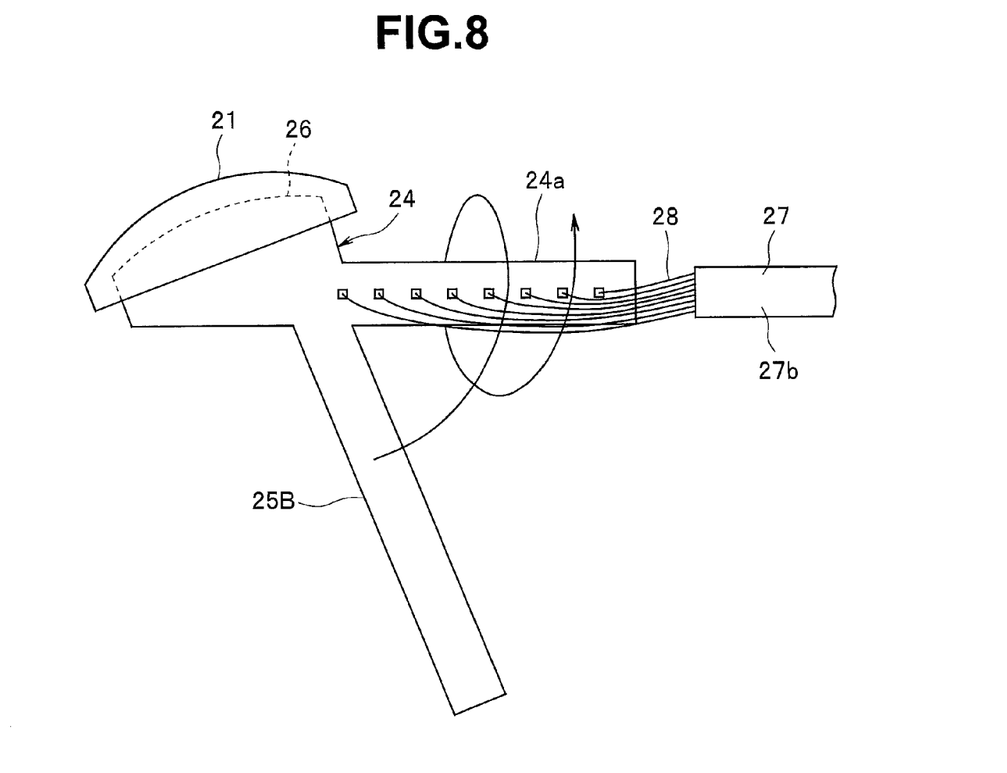
FIG. 8 is a view showing a configuration of a branched flexible portion provided at a rigid flexible substrate, in embodiment 3 of the present invention.
Figure 9:
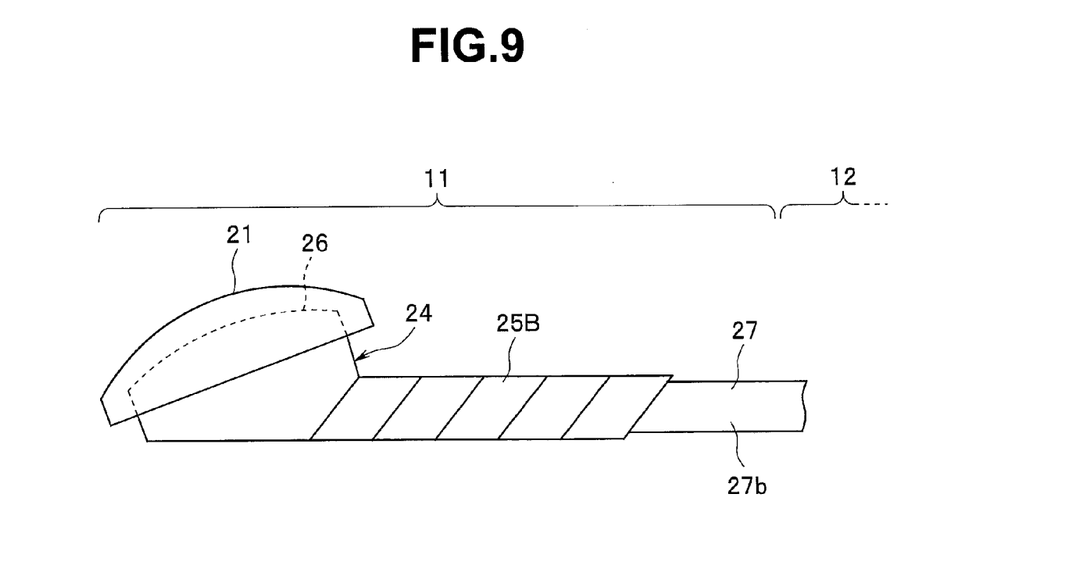
FIG. 9 is a view showing a shape of the rigid flexible substrate at a time of being stored in a rigid portion, in the above described embodiment 3 of the present invention.

FIG. 8 and FIG. 9 show embodiment 3 of the present invention. FIG. 8 is a view showing a configuration of a branched flexible portion 25B that is provided at the rigid flexible substrate 24. FIG. 9 is a view showing a shape of the rigid flexible substrate 24 at a time of being stored in the rigid portion 11.

In embodiment 3, parts similar to those in the aforementioned embodiments 1 and 2 are assigned with the same reference signs, the description thereof will be properly omitted, and only a different point will be mainly described.

It is similar to the aforementioned embodiment 1 that the ultrasound probe 21 is connected to the rigid portion 26 in the rigid flexible substrate 24.

The rigid flexible substrate 24 includes a wiring connection substrate portion 24a that is extensively provided in a band shape toward a proximal end side from the rigid portion 26 to which the ultrasound probe 21 is connected. The wiring connection substrate portion 24a may be configured as a rigid portion, or may be configured as a flexible portion. In the wiring connection substrate portion 24a, at least the wiring layer 32 that is extensively provided from the rigid portion 26 is placed (other layers differ depending on whether the wiring connection substrate portion 24a is configured as a rigid portion or a flexible portion, and the like), and the wiring connection substrate portion 24a includes a wiring connection portion where the signal lines 28 of the cable 27 are electrically connected by soldering or the like.

Furthermore, the rigid flexible substrate 24 of the present embodiment is branched into a plurality of portions, and at least one branch is a branched flexible portion 25B as at least one part of a flexible portion (for example, when the wiring connection substrate portion 24a is configured as the flexible portion, the branched flexible portion 25B becomes a part of the flexible portion, whereas when all portions other than the branched flexible portion 25B are configured as a rigid portion, the branched flexible portion 25B becomes all of the flexible portion).

The branched flexible portion 25B is branched from the ultrasound probe 21 side from the aforementioned wiring connection portion (for example, a distal end side of the wiring connection substrate portion 24a, a proximal end side of the rigid portion 26, or the like), and the shield layer 33 extensively provided from the rigid portion 26 is placed (note that needless to say, the base layer 31 and the insulating layers 34 and 35 are also placed). Further, a branch angle of the branched flexible portion 25B with respect to the wiring connection substrate portion 24a preferably corresponds to the inclination angle θ described in embodiment 1.

After electrical connection of the cable 27 to the wiring connection substrate portion 24a is performed as shown in FIG. 8, the branched flexible portion 25B is wound around the wiring connection substrate portion 24a including a wiring connection portion, and the uncovered portion of the distal end side of the cable 27 as shown in FIG. 9. At this time, since the insulating layers 34 and 35 are provided on a surface of the branched flexible portion 25B, the shield layer 33 of the branched flexible portion 25B does not short-circuit to a soldered portion on the wiring connection substrate portion 24a. Further, it is similar to embodiment 1 described above that the rigid flexible substrate 24 is disposed only in the rigid portion 11, and is not disposed in the bending portion 12.

According to embodiment 3 as above, the branched flexible portion 25B is provided and is wound onto the wiring connection substrate portion 24a, whereby a substantially similar effect to those of embodiments 1 and 2 described above also can be provided.

Embodiment 4

Figure 10:
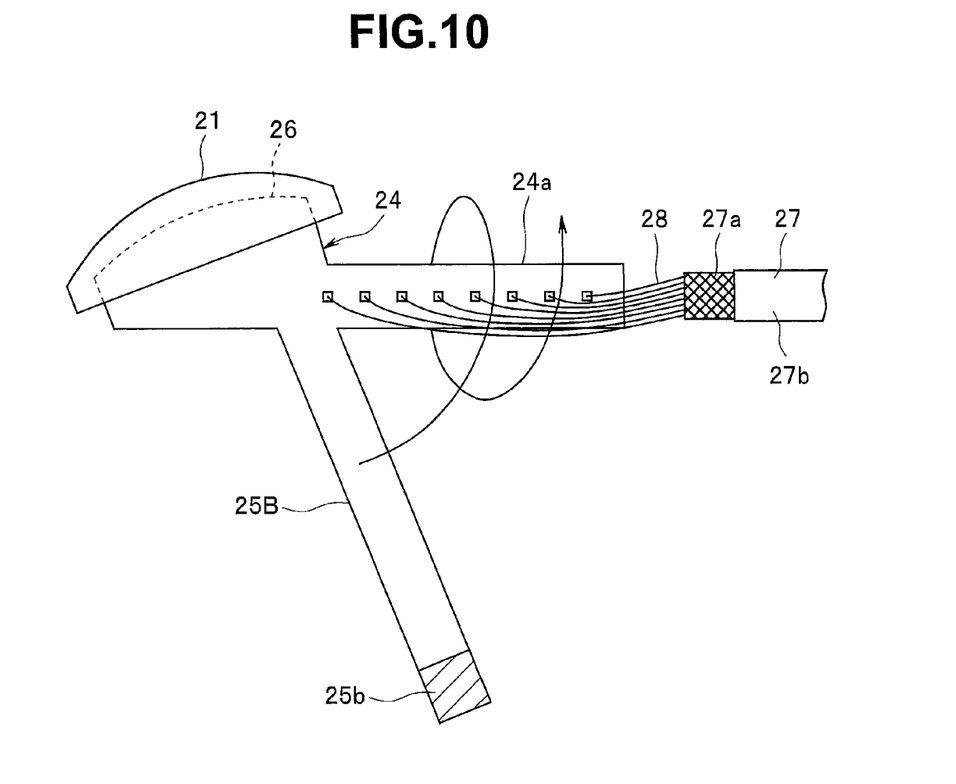
FIG. 10 is a view showing a configuration of a branched flexible portion provided in a rigid flexible substrate, in embodiment 4 of the present invention.
Figure 11:
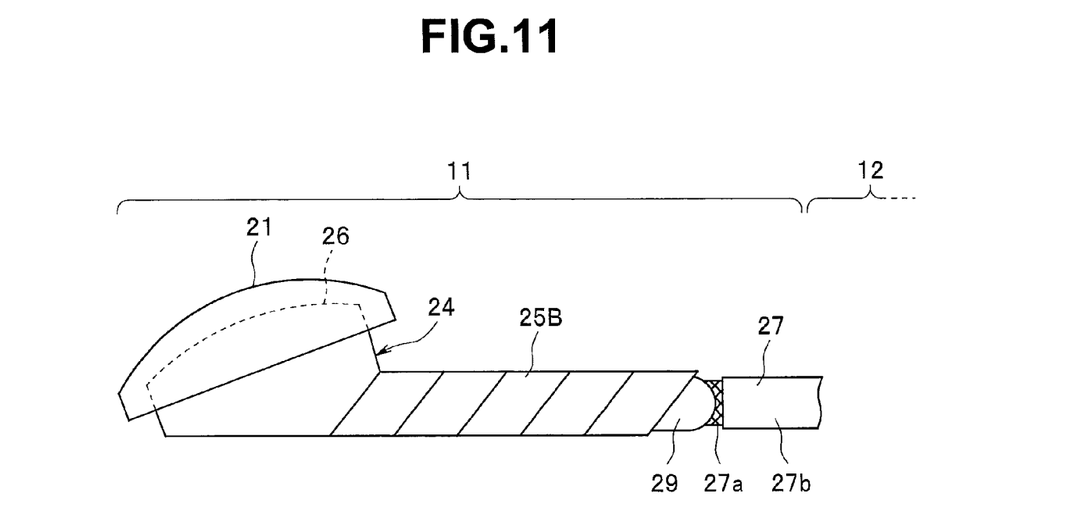
FIG. 11 is a view showing a shape of the rigid flexible substrate at a time of being stored in a rigid portion, in the above described embodiment 4 of the present invention.

FIG. 10 and FIG. 11 show embodiment 4 of the present invention. FIG. 10 is a view showing a configuration of the branched flexible portion 25B provided at the rigid flexible substrate 24. FIG. 11 is a view showing a shape of the rigid flexible substrate 24 at a time when the rigid flexible substrate 24 is stored in the rigid portion 11.

In embodiment 4, parts similar to those in embodiments 1 to 3 described above are assigned with the same reference signs, the description thereof will be properly omitted, and only a different point will be mainly described.

First, the cable 27 includes the overall shield 27a that generally shields the plurality of signal lines 28 similarly to the respective embodiments described above, and in the present embodiment, when the respective signal lines 28 are connected to the wiring connection substrate portion 24a, the cable sheathing cover 27b is removed so that a distal end portion of the overall shield 27a is exposed.

The rigid flexible substrate 24 of the present embodiment is basically configured to be similar to the rigid flexible substrate 24 of embodiment 3 described above, but an electrical connection portion 25b is provided at an end portion that is the farthest away from the wiring connection substrate portion 24a in the branched flexible portion 25B. The electric connection portion 25b is electrically continuous with the shield layer 33 in the branched flexible portion 25B. Accordingly, the electric connection portion 25b is thermally connected to the ultrasound probe 21.

Electrical connection of the cable 27 to the wiring connection substrate portion 24a is performed as shown in FIG. 10, and after the branched flexible portion 25B is wound on the wiring connection substrate portion 24a and the uncovered portion of the distal end side of the cable 27, the electrical connection portion 25b is electrically connected to the overall shield 27a with use of solder 29 or the like. Accordingly, the shield layer 33 is not only connected to the signal line 28 that is connected to a ground, but is also further connected to the overall shield 27a.

By the configuration as above, heat that is generated from the ultrasound probe 21 and is transmitted through the shield layer 33, a current that is generated from electromagnetic waves shielded by the shield layer 33 and the like are transmitted via the signal line 28 connected to the ground and the overall shield 27a.

According to embodiment 4 as above, a substantially similar effect as those of embodiments 1 to 3 described above is provided, and since the shield layer 33 is connected to the ground by a plurality of routes, unnecessary heat and an unnecessary current can be more efficiently transmitted. Accordingly, the cooling effect of, for example, the ultrasound probe 21 can be more enhanced.

Note that the present invention is not limited to the embodiments as described above as they are, but can be embodied with the components being changed within the range without departing from the gist thereof in the implementation stage. Further, various aspects of the invention can be formed by proper combinations of a plurality of components disclosed in the above described embodiments. For example, some components may be deleted from all the components shown in the embodiments. Further, the components throughout the different embodiments may be properly combined. It is a matter of course that various changes and applications can be made within the range without departing from the gist of the invention.

What is claimed is:

1. An ultrasound endoscope, comprising:
an insertion portion that is insertable into an observation site, and is provided with a rigid portion at a distal end side;
an ultrasound probe that is provided at the rigid portion, and has a plurality of ultrasound transducers that transmit and receive ultrasound signals;
a cable for transmitting electrical signals that are inputted to and outputted from the ultrasound probe; and
a rigid flexible substrate that is interposed between the ultrasound probe and the cable to transmit the electrical signals, is configured as a planar member in which a plurality of layers including a wiring layer are stacked, and has a flexible portion configured only by a flexible substrate, and a rigid portion provided with a rigid substrate, by forming a part of the planar member as the flexible substrate which further includes an insulating layer, and by forming the other part of the planar member as the rigid substrate which further includes a rigid layer,
wherein the ultrasound probe is connected to the rigid portion, and
at least a part of the flexible portion is disposed in a spiral shape to surround a wiring connection portion of the cable and the rigid flexible substrate, and an uncovered portion of a distal end side of the cable.

2. The ultrasound endoscope according to claim 1,
wherein the plurality of layers further include a shield layer.

3. The ultrasound endoscope according to claim 1,
wherein the cable is connected to the flexible portion, and
at least a part of the flexible portion is wound on the uncovered portion of the distal end side of the cable.

4. The ultrasound endoscope according to claim 1,
wherein the rigid flexible substrate is divided into a plurality of branches, and at least one branch is a branched flexible portion as at least a part of the flexible portion, and
the branched flexible portion is wound on the wiring connection portion and the uncovered portion of the distal end side of the cable.

5. The ultrasound endoscope according to claim 4,
wherein the plurality of layers further include a shield layer,
the cable includes an overall shield that generally shields a plurality of signal lines,
the branched flexible portion is branched from the ultrasound probe side relative to the wiring connection portion, and has an electrical connection portion that is electrically continuous with the shield layer at an end portion, and the electrical connection portion is electrically connected to the overall shield.

6. The ultrasound endoscope according to claim 5, wherein the shield layer is thermally connected to the ultrasound probe, and includes a function of transmitting heat generated from the ultrasound probe.

7. The ultrasound endoscope according to claim 1, wherein the insertion portion includes a bendable bending portion connectively provided at a proximal end side of the rigid portion, and the rigid flexible substrate is disposed only in the rigid portion.

* * * * *